(12) United States Patent
Schweikert et al.

(10) Patent No.: US 8,257,325 B2
(45) Date of Patent: Sep. 4, 2012

(54) VENOUS ACCESS PORT WITH MOLDED AND/OR RADIOPAQUE INDICIA

(75) Inventors: Timothy M. Schweikert, Levittown, PA (US); Raymond R. Bizup, Feasterville, PA (US); Kevin E. Sanford, Chalfont, PA (US); Kenneth M. Zinn, Westport, CT (US)

(73) Assignees: Medical Components, Inc., Harleysville, PA (US); Innovative Medical Devices, LLC, Westport, CT (US)

( * ) Notice: Subject to any disclaimer, the term of this patent is extended or adjusted under 35 U.S.C. 154(b) by 294 days.

(21) Appl. No.: 12/143,377

(22) Filed: Jun. 20, 2008

(65) Prior Publication Data

US 2008/0319399 A1 Dec. 25, 2008

Related U.S. Application Data

(60) Provisional application No. 60/936,491, filed on Jun. 20, 2007.

(51) Int. Cl.
*A61M 37/00* (2006.01)
*A61K 9/22* (2006.01)

(52) U.S. Cl. ........... 604/288.01; 604/891.1; 604/288.02; 604/288.04

(58) Field of Classification Search ............... 604/891.1, 604/288.01, 288.02, 536, 175
See application file for complete search history.

(56) References Cited

U.S. PATENT DOCUMENTS

| | | | |
|---|---|---|---|
| 574,387 A | 1/1897 | Buckler | |
| 611,357 A | 9/1898 | Dembinski | |
| 966,696 A | 8/1910 | Merrill | |
| 1,713,267 A | 5/1929 | Crowley | |
| 2,029,553 A | 2/1936 | Bartschi et al. | |
| 2,433,480 A | 12/1947 | Rendich | |

(Continued)

FOREIGN PATENT DOCUMENTS

DE 84 37 873 U1 2/1986

(Continued)

OTHER PUBLICATIONS

BARD Access System product drawings representative of the BARD Access System products on the market on or around Mar. 1995 as indicated by the BARD Access Systems Mar. 21, 1995 Product Release to Market form for "M.R.I. Port with 8 Fr. ChronoFlex® Catheter," "M.R.I. Port with 8 Fr. ChronoFlex Catheter with Intro-Eze™," "M.R.I. Port with 8 Fr. Chrono-Flex Catheter and Peel Apart," "M.R.I. Port with 8 Fr. ChronoFlex Catheter Demo Kit," 6 pages.

(Continued)

*Primary Examiner* — Kevin C Sirmons
*Assistant Examiner* — Bradley Thomas, Jr.
(74) *Attorney, Agent, or Firm* — Blank Rome LLP (57) ABSTRACT

A venous access port assembly having a housing base with a discharge port, a septum and a cap. An interior reservoir is defined by a well in the housing base and a bottom of the septum, and a passageway extends from the reservoir through the discharge port. The housing base includes a base flange having integrally molded therein indicia identifying an attribute of the assembly. The indicia could be formed of base flange material, or could be formed by voids in the base flange material. If of plastic material, the molded indicia could be applied with a radiopaque agent, thereby allowing the indicia ("CT") to appear on an X-ray of the patient in a manner informing a practitioner of a particular attribute of the assembly.

22 Claims, 5 Drawing Sheets

U.S. PATENT DOCUMENTS

| | | |
|---|---|---|
| 2,891,689 A | 6/1959 | Gould |
| D198,453 S | 6/1964 | Weichselbaum |
| 3,293,663 A | 12/1966 | Cronin |
| 3,341,417 A | 9/1967 | Sinaiko |
| 3,518,428 A | 6/1970 | Ring |
| 3,529,633 A | 9/1970 | Vaillancourt |
| 3,643,358 A | 2/1972 | Morderosian |
| 3,829,904 A | 8/1974 | Ling et al. |
| 3,831,583 A | 8/1974 | Edmunds, Jr. et al. |
| 3,840,009 A | 10/1974 | Michaels et al. |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,168,586 A | 9/1979 | Samis |
| 4,190,040 A | 2/1980 | Schulte |
| 4,190,057 A | 2/1980 | Hill et al. |
| 4,194,122 A | 3/1980 | Mitchell et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,450,592 A | 5/1984 | Niederer et al. |
| 4,450,985 A | 5/1984 | Beard |
| 4,456,011 A | 6/1984 | Warnecke et al. |
| 4,469,483 A | 9/1984 | Becker et al. |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,046 A | 12/1985 | Groshong et al. |
| 4,571,749 A | 2/1986 | Fischell |
| 4,576,595 A | 3/1986 | Aas et al. |
| 4,587,954 A | 5/1986 | Haber |
| 4,612,877 A | 9/1986 | Hayes et al. |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton, Jr. et al. |
| 4,684,365 A | 8/1987 | Reinicke |
| 4,685,447 A | 8/1987 | Iversen et al. |
| 4,685,905 A | 8/1987 | Jeanneret nee Aab |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stöber et al. |
| 4,710,174 A | 12/1987 | Moden et al. |
| 4,718,894 A | 1/1988 | Lazorthes |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,892,518 A | 1/1990 | Cupp et al. |
| 4,904,241 A | 2/1990 | Bark |
| 4,905,709 A | 3/1990 | Bieganski et al. |
| 4,909,250 A | 3/1990 | Smith |
| 4,915,690 A | 4/1990 | Cone et al. |
| 4,928,298 A | 5/1990 | Tanaka et al. |
| 4,929,236 A | 5/1990 | Sampson |
| 4,955,861 A | 9/1990 | Enegren et al. |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,009,644 A | 4/1991 | McDonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,084,015 A | 1/1992 | Moriuchi |
| 5,085,216 A | 2/1992 | Henley, Jr. et al. |
| 5,090,066 A | 2/1992 | Schoepe et al. |
| 5,092,849 A | 3/1992 | Sampson |
| 5,108,317 A | 4/1992 | Beinhaur et al. |
| 5,108,377 A | 4/1992 | Cone et al. |
| 5,112,301 A | 5/1992 | Fenton, Jr. et al. |
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,171,228 A | 12/1992 | McDonald |
| 5,176,653 A | 1/1993 | Metals et al. |
| 5,176,662 A | 1/1993 | Bartholomew et al. |
| 5,178,612 A | 1/1993 | Fenton, Jr. |
| 5,185,003 A | 2/1993 | Brethauer |
| 5,189,690 A | 2/1993 | Samuel |
| 5,193,106 A | 3/1993 | DeSena |
| 5,195,122 A | 3/1993 | Fabian |
| 5,195,123 A | 3/1993 | Clement |
| 5,201,715 A | 4/1993 | Masters |
| 5,203,771 A | 4/1993 | Melker et al. |
| 5,203,777 A | 4/1993 | Lee |
| 5,213,574 A | 5/1993 | Tucker |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,263,930 A | 11/1993 | Ensminger |
| 5,281,205 A | 1/1994 | McPherson |
| 5,290,263 A | 3/1994 | Wigness et al. |
| 5,295,658 A | 3/1994 | Atkinson et al. |
| 5,299,253 A | 3/1994 | Wessels |
| 5,309,863 A | 5/1994 | Leeb, Jr. |
| 5,312,337 A | 5/1994 | Flaherty et al. |
| 5,318,545 A | 6/1994 | Tucker |
| 5,320,100 A | 6/1994 | Herweck et al. |
| 5,328,480 A | 7/1994 | Melker et al. |
| 5,332,398 A | 7/1994 | Miller et al. |
| 5,334,153 A | 8/1994 | McIntyre et al. |

| Patent No. | Date | Inventor(s) |
|---|---|---|
| 5,336,194 A | 8/1994 | Polaschegg et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard |
| 5,383,233 A | 1/1995 | Russell |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,397,329 A | 3/1995 | Allen |
| 5,399,168 A | 3/1995 | Wadsworth, Jr. et al. |
| 5,405,402 A | 4/1995 | Dye et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,433,480 A | 7/1995 | Gresham et al. |
| 5,456,698 A | 10/1995 | Byland et al. |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,527,277 A | 6/1996 | Ensminger et al. |
| 5,527,307 A | 6/1996 | Srisathapat et al. |
| 5,531,684 A | 7/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,575,770 A | 11/1996 | Melsky et al. |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai et al. |
| 5,637,102 A | 6/1997 | Tolkoff et al. |
| 5,638,832 A | 6/1997 | Singer et al. |
| 5,647,855 A | 7/1997 | Trooskin |
| 5,662,612 A | 9/1997 | Niehoff |
| 5,676,146 A | 10/1997 | Scarborough |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch, Jr. et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,810,789 A | 9/1998 | Powers et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,935 A | 11/1998 | Ashton et al. |
| 5,840,063 A | 11/1998 | Flaherty |
| 5,843,069 A | 12/1998 | Butler et al. |
| 5,853,394 A | 12/1998 | Tolkoff et al. |
| 5,868,702 A | 2/1999 | Stevens et al. |
| 5,882,353 A | 3/1999 | VanBeek et al. |
| 5,895,424 A | 4/1999 | Steele, Sr. et al. |
| 5,906,596 A | 5/1999 | Tallarida |
| 5,908,414 A | 6/1999 | Otto et al. |
| 5,913,998 A | 6/1999 | Butler et al. |
| 5,916,263 A | 6/1999 | Goicoechea et al. |
| 5,925,017 A | 7/1999 | Kriesel et al. |
| 5,925,030 A | 7/1999 | Gross et al. |
| 5,928,197 A | 7/1999 | Niehoff |
| 5,931,829 A | 8/1999 | Burbank et al. |
| 5,935,084 A | 8/1999 | Southworth |
| 5,944,023 A | 8/1999 | Johnson et al. |
| 5,944,688 A | 8/1999 | Lois |
| 5,944,712 A | 8/1999 | Frassica et al. |
| 5,947,953 A | 9/1999 | Ash et al. |
| 5,951,512 A | 9/1999 | Dalton |
| 5,951,522 A | 9/1999 | Rosato et al. |
| 5,954,687 A | 9/1999 | Baudino |
| 5,957,890 A | 9/1999 | Mann et al. |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,077,256 A | 6/2000 | Lin et al. |
| 6,086,555 A | 7/2000 | Eliasen |
| 6,090,066 A | 7/2000 | Schnell |
| 6,102,884 A | 8/2000 | Squitieri |
| 6,113,572 A | 9/2000 | Gailey et al. |
| 6,120,492 A | 9/2000 | Finch et al. |
| 6,161,033 A | 12/2000 | Kuhn |
| 6,171,198 B1 | 1/2001 | Lizama Troncoso et al. |
| 6,171,298 B1 | 1/2001 | Matsuura et al. |
| 6,174,330 B1 | 1/2001 | Stinson |
| 6,190,352 B1 | 2/2001 | Haarala et al. |
| 6,193,684 B1 | 2/2001 | Burbank et al. |
| 6,198,807 B1 | 3/2001 | DeSena |
| 6,203,570 B1 | 3/2001 | Baeke |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,269,148 B1 | 7/2001 | Jessop et al. |
| 6,287,293 B1 * | 9/2001 | Jones et al. ............... 604/891.1 |
| 6,290,677 B1 | 9/2001 | Arai et al. |
| 6,302,875 B1 | 10/2001 | Makower et al. |
| 6,305,413 B1 | 10/2001 | Fischer et al. |
| D450,115 S | 11/2001 | Bertheas |
| 6,332,874 B1 | 12/2001 | Eliasen et al. |
| 6,347,241 B2 | 2/2002 | Burbank et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,450,937 B1 | 9/2002 | Mercereau et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,582,418 B1 | 6/2003 | Verbeek et al. |
| 6,613,002 B1 | 9/2003 | Clark et al. |
| 6,613,662 B2 | 9/2003 | Wark et al. |
| 6,626,936 B2 | 9/2003 | Stinson |
| 6,629,950 B1 | 10/2003 | Levin |

| | | | | | | |
|---|---|---|---|---|---|---|
| 6,632,217 B2 | 10/2003 | Harper et al. | | 2001/0056266 A1 | 12/2001 | Tallarida et al. |
| 6,652,486 B2 | 11/2003 | Bialecki et al. | | 2002/0095205 A1 | 7/2002 | Edwin et al. |
| 6,652,503 B1 | 11/2003 | Bradley | | 2002/0138068 A1 | 9/2002 | Watson et al. |
| 6,676,633 B2 | 1/2004 | Smith et al. | | 2002/0173769 A1 | 11/2002 | Gray et al. |
| 6,697,664 B2 | 2/2004 | Kienzle, III et al. | | 2003/0010929 A1 | 1/2003 | Priewe et al. |
| 6,705,316 B2 | 3/2004 | Blythe et al. | | 2003/0028173 A1 | 2/2003 | Forsberg |
| 6,719,721 B1 | 4/2004 | Okazaki et al. | | 2003/0130627 A1 | 7/2003 | Smith et al. |
| 6,719,739 B2 | 4/2004 | Verbeek et al. | | 2003/0139812 A1 | 7/2003 | Garcia et al. |
| 6,738,531 B1 | 5/2004 | Funahashi | | 2003/0181878 A1 | 9/2003 | Tallarida et al. |
| 6,755,842 B2 | 6/2004 | Kanner et al. | | 2003/0191452 A1 | 10/2003 | Meglin et al. |
| 6,758,841 B2 | 7/2004 | Haarala et al. | | 2004/0002693 A1 | 1/2004 | Bright et al. |
| 6,767,356 B2 | 7/2004 | Kanner et al. | | 2004/0006316 A1 | 1/2004 | Patton |
| 6,784,783 B2 | 8/2004 | Scoggin et al. | | 2004/0019356 A1 | 1/2004 | Fraser et al. |
| 6,826,257 B2 | 11/2004 | Sayre et al. | | 2004/0020462 A1 | 2/2004 | Sauler et al. |
| 6,852,106 B2 | 2/2005 | Watson et al. | | 2004/0044306 A1 | 3/2004 | Lynch et al. |
| 6,878,136 B2 | 4/2005 | Fleury et al. | | 2004/0054352 A1 | 3/2004 | Adams et al. |
| 6,878,137 B2 | 4/2005 | Benchetrit | | 2004/0056266 A1 | 3/2004 | Suh et al. |
| 6,949,084 B2 | 9/2005 | Marggi et al. | | 2004/0064110 A1 | 4/2004 | Forsell |
| 6,962,580 B2 | 11/2005 | Adams et al. | | 2004/0073196 A1 | 4/2004 | Adams et al. |
| 6,994,315 B2 | 2/2006 | Ryan et al. | | 2004/0093069 A1 | 5/2004 | Priewe et al. |
| 6,997,914 B2 | 2/2006 | Smith et al. | | 2004/0106878 A1 | 6/2004 | Skujins et al. |
| 7,008,377 B2 | 3/2006 | Beane et al. | | 2004/0106891 A1 | 6/2004 | Langan et al. |
| 7,008,412 B2 | 3/2006 | Maginot | | 2004/0157952 A1 | 8/2004 | Soffiati et al. |
| 7,016,456 B2 | 3/2006 | Basu et al. | | 2004/0158207 A1 | 8/2004 | Hunn et al. |
| 7,018,361 B2 | 3/2006 | Gillespie, Jr. et al. | | 2004/0167543 A1 | 8/2004 | Mazzocchi et al. |
| 7,044,942 B2 | 5/2006 | Jolly et al. | | 2004/0176743 A1 | 9/2004 | Morris et al. |
| 7,056,316 B1 | 6/2006 | Burbank et al. | | 2004/0199129 A1 | 10/2004 | DiMatteo |
| 7,070,591 B2 | 7/2006 | Adams et al. | | 2004/0199220 A1 | 10/2004 | Cantlon |
| 7,072,704 B2 | 7/2006 | Bucholz | | 2004/0204692 A1 | 10/2004 | Eliasen |
| 7,074,232 B2 | 7/2006 | Kanner et al. | | 2004/0225254 A1 | 11/2004 | Tanaka et al. |
| 7,083,593 B2 | 8/2006 | Stultz | | 2004/0254536 A1 | 12/2004 | Conlon et al. |
| 7,108,686 B2 | 9/2006 | Burke et al. | | 2004/0254537 A1 | 12/2004 | Conlon et al. |
| 7,123,690 B1 | 10/2006 | Brown et al. | | 2005/0049553 A1 | 3/2005 | Triplett et al. |
| 7,127,040 B2 | 10/2006 | Sayre et al. | | 2005/0070875 A1 | 3/2005 | Kulessa |
| 7,131,962 B1 | 11/2006 | Estabrook et al. | | 2005/0075614 A1 | 4/2005 | Bunodiere et al. |
| 7,140,769 B2 | 11/2006 | Kay | | 2005/0113806 A1 | 5/2005 | De Carvalho et al. |
| 7,191,011 B2 | 3/2007 | Cantlon | | 2005/0131352 A1 | 6/2005 | Conlon et al. |
| 7,198,631 B2 | 4/2007 | Kanner et al. | | 2005/0148866 A1 | 7/2005 | Gunderson |
| 7,214,207 B2 | 5/2007 | Lynch et al. | | 2005/0148956 A1 | 7/2005 | Conlon et al. |
| 7,214,215 B2 | 5/2007 | Heinzerling et al. | | 2005/0148957 A1 | 7/2005 | Girard et al. |
| 7,223,257 B2 | 5/2007 | Shubayev et al. | | 2005/0152841 A1 | 7/2005 | Sayre et al. |
| 7,229,417 B2 | 6/2007 | Foerster et al. | | 2005/0171502 A1 | 8/2005 | Daly et al. |
| 7,235,067 B2 | 6/2007 | Morris et al. | | 2005/0182857 A1 | 8/2005 | Kong |
| D546,440 S | 7/2007 | Burnside | | 2005/0209573 A1 | 9/2005 | Brugger et al. |
| 7,242,982 B2 | 7/2007 | Singhal et al. | | 2005/0215874 A1 | 9/2005 | Wang et al. |
| 7,252,469 B2 | 8/2007 | Zaluzec et al. | | 2005/0215876 A1 | 9/2005 | Chen et al. |
| 7,252,649 B2 | 8/2007 | Sherry | | 2005/0241203 A1 | 11/2005 | Lizotte et al. |
| 7,261,705 B2 | 8/2007 | Edoga et al. | | 2005/0256451 A1 | 11/2005 | Adams et al. |
| D554,253 S | 10/2007 | Kornerup | | 2005/0256500 A1 | 11/2005 | Fujii |
| 7,275,682 B2 | 10/2007 | Excoffier et al. | | 2005/0277899 A1 | 12/2005 | Conlon et al. |
| 7,276,075 B1 | 10/2007 | Callas et al. | | 2005/0283119 A1 | 12/2005 | Uth et al. |
| D556,153 S | 11/2007 | Burnside | | 2006/0009788 A1 | 1/2006 | Freeman et al. |
| 7,306,579 B2 | 12/2007 | Fujii | | 2006/0017341 A1 | 1/2006 | Hahn et al. |
| 7,311,702 B2 | 12/2007 | Tallarida et al. | | 2006/0084929 A1 | 4/2006 | Eliasen |
| 7,318,816 B2 | 1/2008 | Bobroff et al. | | 2006/0089619 A1 | 4/2006 | Ginggen |
| 7,318,818 B2 | 1/2008 | Yashiro et al. | | 2006/0100592 A1 | 5/2006 | Eliasen |
| 7,322,953 B2 | 1/2008 | Redinger | | 2006/0116648 A1 | 6/2006 | Hamatake |
| D562,443 S | 2/2008 | Zinn et al. | | 2006/0173410 A1 | 8/2006 | Moberg et al. |
| 7,331,130 B2 | 2/2008 | Schweikert | | 2006/0173424 A1 | 8/2006 | Conlon |
| 7,331,948 B2 | 2/2008 | Skarda | | 2006/0178647 A1* | 8/2006 | Stats .................. 604/288.01 |
| 7,333,013 B2 | 2/2008 | Berger | | 2006/0184141 A1 | 8/2006 | Smith et al. |
| D564,449 S | 3/2008 | Dewberry | | 2006/0184142 A1 | 8/2006 | Schon et al. |
| 7,347,838 B2 | 3/2008 | Kulli | | 2006/0217359 A1 | 9/2006 | Wentworth et al. |
| 7,347,843 B2 | 3/2008 | Adams et al. | | 2006/0217659 A1 | 9/2006 | Patton |
| 7,351,233 B2 | 4/2008 | Parks | | 2006/0224128 A1 | 10/2006 | Lurvey et al. |
| 7,377,915 B2 | 5/2008 | Rasmussen et al. | | 2006/0224129 A1* | 10/2006 | Beasley et al. .......... 604/288.01 |
| D574,950 S | 8/2008 | Zawacki et al. | | 2006/0247584 A1 | 11/2006 | Sheetz et al. |
| 7,413,564 B2 | 8/2008 | Morris et al. | | 2006/0253076 A1 | 11/2006 | Butts et al. |
| D578,203 S | 10/2008 | Bizup | | 2006/0264898 A1* | 11/2006 | Beasley et al. ................ 604/506 |
| 7,445,614 B2 | 11/2008 | Bunodiere et al. | | 2007/0007839 A1 | 1/2007 | Lin |
| D582,032 S | 12/2008 | Bizup et al. | | 2007/0049876 A1 | 3/2007 | Patton |
| 7,465,847 B2 | 12/2008 | Fabian | | 2007/0055290 A1 | 3/2007 | Lober |
| D595,892 S | 7/2009 | Smith et al. | | 2007/0073250 A1 | 3/2007 | Schneiter |
| 7,563,025 B2 | 7/2009 | Kay | | 2007/0078391 A1 | 4/2007 | Wortley et al. |
| 7,713,251 B2 | 5/2010 | Tallarida et al. | | 2007/0078416 A1 | 4/2007 | Eliasen |
| 7,833,281 B2 | 11/2010 | Lehman et al. | | 2007/0078432 A1 | 4/2007 | Halseth et al. |
| 2001/0016717 A1 | 8/2001 | Haarala et al. | | 2007/0083156 A1 | 4/2007 | Muto et al. |
| 2001/0051766 A1 | 12/2001 | Gazdzinski | | 2007/0149920 A1 | 6/2007 | Michels et al. |
| 2001/0053889 A1 | 12/2001 | Marggi et al. | | 2007/0149921 A1 | 6/2007 | Michels et al. |

| | | | |
|---|---|---|---|
| 2007/0161958 A1 | 7/2007 | Glenn | |
| 2007/0161985 A1 | 7/2007 | Demakas et al. | |
| 2007/0179456 A1 | 8/2007 | Glenn | |
| 2007/0185462 A1 | 8/2007 | Byrum | |
| 2007/0191773 A1 | 8/2007 | Wojcik | |
| 2007/0208313 A1 | 9/2007 | Conlon et al. | |
| 2007/0219510 A1 | 9/2007 | Zinn et al. | |
| 2007/0233017 A1 | 10/2007 | Zinn et al. | |
| 2007/0233018 A1 | 10/2007 | Bizup et al. | |
| 2007/0255234 A1 | 11/2007 | Haase et al. | |
| 2007/0270691 A1 | 11/2007 | Bailey et al. | |
| 2007/0270770 A1 | 11/2007 | Bizup | |
| 2007/0276344 A1 | 11/2007 | Bizup et al. | |
| 2007/0299408 A1 | 12/2007 | Alferness et al. | |
| 2008/0004642 A1 | 1/2008 | Birk et al. | |
| 2008/0008654 A1 | 1/2008 | Clarke et al. | |
| 2008/0015701 A1 | 1/2008 | Garcia et al. | |
| 2008/0039820 A1 | 2/2008 | Sommers et al. | |
| 2008/0048855 A1 | 2/2008 | Berger | |
| 2008/0108949 A1 | 5/2008 | Beasley et al. | |
| 2008/0114308 A1 | 5/2008 | di Palma et al. | |
| 2008/0138387 A1 | 6/2008 | Machiraju | |
| 2008/0140025 A1 | 6/2008 | Sheetz et al. | |
| 2008/0208236 A1 | 8/2008 | Hobbs et al. | |
| 2008/0281279 A1 | 11/2008 | Hoendervoogt et al. | |
| 2008/0319398 A1 | 12/2008 | Bizup | |
| 2008/0319399 A1 | 12/2008 | Schweikert et al. | |
| 2008/0319405 A1 | 12/2008 | Bizup | |
| 2009/0024024 A1 | 1/2009 | Zinn | |
| 2009/0024098 A1 | 1/2009 | Bizup et al. | |
| 2009/0035582 A1 | 2/2009 | Nakatani et al. | |
| 2009/0118683 A1 | 5/2009 | Hanson et al. | |
| 2009/0156928 A1 | 6/2009 | Evans et al. | |
| 2009/0171436 A1 | 7/2009 | Casanova et al. | |
| 2009/0204072 A1 | 8/2009 | Amin et al. | |
| 2009/0204074 A1 | 8/2009 | Powers et al. | |
| 2009/0221976 A1 | 9/2009 | Linden | |
| 2009/0227862 A1 | 9/2009 | Smith et al. | |
| 2009/0227951 A1 | 9/2009 | Powers et al. | |
| 2010/0004735 A1 | 1/2010 | Yang et al. | |
| 2010/0042073 A1 | 2/2010 | Oster et al. | |
| 2010/0069743 A1 | 3/2010 | Sheetz et al. | |
| WO | WO 2006/134100 A1 | 12/2006 | |
| WO | WO 2007/079024 A2 | 7/2007 | |
| WO | WO 2007/092210 A1 | 8/2007 | |
| WO | WO 2007/094898 A2 | 8/2007 | |
| WO | WO 2007/098771 A2 | 9/2007 | |
| WO | WO 2007/109164 A2 | 9/2007 | |
| WO | WO 2007136538 A2 | 11/2007 | |
| WO | WO 2008008126 A2 | 1/2008 | |
| WO | WO 2008019236 A1 | 2/2008 | |
| WO | WO 2008048361 A1 | 4/2008 | |
| WO | WO 2008063226 A2 | 5/2008 | |
| WO | WO 2007/126645 A2 | 11/2008 | |
| WO | WO 2008/147760 A1 | 12/2008 | |
| WO | WO 2009/002839 A1 | 12/2008 | |
| WO | WO 2008157763 A1 | 12/2008 | |
| WO | WO 2009012385 A1 | 1/2009 | |
| WO | WO 2009012395 A1 | 1/2009 | |
| WO | WO 2009035582 A1 | 3/2009 | |
| WO | WO 2009/046725 A1 | 4/2009 | |
| WO | WO 2009046439 A2 | 4/2009 | |
| WO | WO 2009/108669 A1 | 9/2009 | |

FOREIGN PATENT DOCUMENTS

| | | |
|---|---|---|
| DE | 34 47 202 A1 | 7/1986 |
| DE | 197 45 654 A1 | 4/1999 |
| EP | 0619101 A1 | 10/1994 |
| EP | 0 750 520 B1 | 8/2000 |
| FR | 2 569 987 A1 | 3/1986 |
| FR | 2 586 569 A1 | 3/1987 |
| GB | 2 203 342 A | 10/1988 |
| JP | 2500388 Y2 | 6/1996 |
| JP | 08-168322 A | 7/1996 |
| JP | 2602109 B2 | 4/1997 |
| JP | 2003-102831 A | 4/2003 |
| JP | 2004-350937 A | 12/2004 |
| JP | 2006-025948 | 2/2006 |
| WO | WO 8600213 A1 | 1/1986 |
| WO | WO 9305730 A1 | 4/1993 |
| WO | 95/14504 A1 | 6/1995 |
| WO | WO 9701370 A1 | 1/1997 |
| WO | 97/06845 A1 | 2/1997 |
| WO | 97/11726 A1 | 4/1997 |
| WO | WO 98/17337 A1 | 4/1998 |
| WO | WO 9942166 A1 | 8/1999 |
| WO | WO 0033901 A1 | 6/2000 |
| WO | 00/47264 A1 | 8/2000 |
| WO | WO 0247549 A1 | 6/2002 |
| WO | 02/100480 A2 | 12/2002 |
| WO | 03/037215 A2 | 5/2003 |
| WO | 03/086508 A1 | 10/2003 |
| WO | WO 2004004800 A2 | 1/2004 |
| WO | WO 2004/071555 A2 | 8/2004 |
| WO | WO 2005/037055 A2 | 4/2005 |
| WO | WO 2004/091434 A2 | 10/2005 |
| WO | WO 2006/078915 A2 | 7/2006 |
| WO | WO 2006096686 A1 | 9/2006 |
| WO | WO 2006116438 A2 | 11/2006 |
| WO | WO 2006/130133 A1 | 12/2006 |

OTHER PUBLICATIONS

BioEnterics® LAP-BAND® "Adjustable Gastric Banding System" by Inamed Health, Product Brochure, Dec. 2003, 22 pages.

Cardiovascular and Interventional Radiology, Review Article, "Central Venous Access Catheters: Radiological Management of Complications," by U.K. Teichgraber et al., published online Jul. 31, 2003, 13 pages.

European Patent Office Communication, dated Dec. 15, 2005, for Application No. 99 964 086.5-1257, Applicant STD Manufacturing, Inc., 9 pages.

European Patent Office Communication, dated Mar. 1, 2005, for EP Application No. 99 964 086.5-1257, Applicant STD Manufacturing, Inc., 4 pages.

European Patent Office Communication, dated Mar. 30, 2005, for Application No. 99 964 086.5-1257, Applicant STD Manufacturing, Inc., 3 pages.

European Patent Office Communication, dated Sep. 2, 2008, for Application No. 06 751 411.7-1526, Applicant C.R. Bard, Inc., 4 pages.

LaMaitre Vascular "Port Implantations: using the OptiLock Implantable Port," product information, available at http://www.lemaitre.com/specs_pop.asp, last accessed Apr. 2003, 14 pages.

LAP-BAND AP™ "System with Adjustable Gastric Banding system with OMNIFORM™ Design," Product Brochure, Jul. 2007, 16 pages.

LAP-BAND® "Adjustable Gastric Banding System" by BioEnterics Corporation, Product Brochure, 12 pages.

Lap-Band® System Fact Sheet, © 2007 Allergan, Inc., 2 pages.

MedComp "PortCT Technology", display at SIR Conference, Toronto, Canada, (Mar. 2006), 1 page.

Nucleus Cochlear Implant Systems; User Manual for the ESPrit 3G speech processor and accessories, available at http://www.cochlearamericas.com/PDFs/UserManualSprint.pdf, Issue 2, Dec. 2001, 2 pages.

Oct. 22, 2009 Declaration of Kelly Christian, Director of Product Development at BARD Access Systems, Inc, in support of and depicting a product on the market by Quinton Company approximately ten years prior to Oct. 22, 2009, 1 page.

Port-A-Cath® "Implantable Epidural, Aterial and Peritonial Access Systems," Internet Product Listing of Nov. 19, 2000 archived at http://web.archive.org/web/20001119035900/www.deltec.com/cPacspl.htm, last accessed Oct. 17, 2009, 2 pages.

Port-A-Cath® "Many Port-A-Cath® System Choices," Product Brochure, © 1996 SIMS Deltec, Inc., 5 pages.

Port-A-Cath® "Single-lumen Implantable Vascular Access Systems," Product Specifications, 2004 Smith Medical, 4 pages.

Rappolt, Richard T., et al., "Radiopaque Codification and X-ray identification of Ingested Drugs," Ingestive Radiology, May-Jun. 1966, 4 pages.

Shah, Tilak M. "Radiopaque Polymer Formulations for Medical Devices." Medical Device and Diagnostic Industry, Mar. 2000, 6 pages.

Urquiola, Javier, et al., "Using Lead Foil as a Radiopaque Marker for Computerized Tomography Imaging When Implant Treatment Planning," The Journal of Prosthetic Dentistry, vol. 77, No. 2, Feb. 1997, pp. 227-228.
PCT/US06/008022 International Search Report, mailed Jul. 5, 2006, 2 pages.
PCT/US06/015695 International Search Report, mailed Jan. 11, 2007, 6 pages.
PCT/US06/49007 International Search Report, mailed Oct. 1, 2007, 2 pages.
PCT/US06/49007 Written Opinion, mailed Oct. 1, 2007, 4 pages.
PCT/US07/006776 International Search Report, mailed Dec. 18, 2007, 1 page.
PCT/US07/006776 Written Opinion, mailed Dec. 18, 2007, 3 pages.
PCT/US08/067679 International Search Report, mailed Sep. 30, 2008, 3 pages.
PCT/US08/067679 Written Opinion, mailed Sep. 30, 2008, 4 pages.
PCT/US08/070330 International Search Report, mailed Dec. 1, 2008, 5 pages.
PCT/US08/070330 Written Opinion, mailed Dec. 1, 2008, 5 pages.
PCT/US08/070345 International Search Report, mailed Dec. 1, 2008, 5 pages.
PCT/US08/070345 Written Opinion, mailed Dec. 1, 2008, 6 pages.
U.S. Appl. No. 10/374,000, Advisory Action, mailed Jan. 23, 2007, 3 pages.
U.S. Appl. No. 10/374,000, Office Action, mailed Aug. 28, 2007, 8 pages.
U.S. Appl. No. 10/374,000, Office Action, mailed Feb. 13, 2006, 7 pages.
U.S. Appl. No. 10/374,000, Office Action, mailed Feb. 28, 2007, 8 pages.
U.S. Appl. No. 10/374,000, Office Action, mailed Jul. 28, 2006, 8 pages.
U.S. Appl. No. 10/374,000, Office Action, mailed Mar. 20, 2008, 6 pages.
U.S. Appl. No. 10/374,000, Office Action, mailed May 20, 2009, 9 pages.
U.S. Appl. No. 10/374,000, Office Action, mailed Sep. 30, 2008, 7 pages.
U.S. Appl. No. 10/374,000, Response to Office Action, filed Dec. 28, 2006, 9 pages.
U.S. Appl. No. 10/374,000, Response to Office Action, filed Jun. 20, 2008, 8 pages.
U.S. Appl. No. 10/374,000, Response to Office Action, filed Mar. 30, 2009, 11 pages.
U.S. Appl. No. 10/374,000, Response to Office Action, filed May 12, 2006, 7 pages.
U.S. Appl. No. 10/374,000, Response to Office Action, filed May 29, 2007, 2006, 11 pages.
U.S. Application No. 10/374,000, Response to Office Action, filed Oct. 31, 2007, 8 pages.
U.S. Application No. 10/374,000, Response to Office Action, filed Sepember 21, 2009, 13 pages.
U.S. Appl. No. 11/320,223, Office Action, mailed Feb. 13, 2008, 11 pages.
U.S. Appl. No. 11/320,223, Office Action, mailed Sep. 18, 2008, 7 pages.
U.S. Appl. No. 11/368,954, Preliminary Amendment, filed Dec. 19, 2007, 9 pages.
U.S. Appl. No. 11/380,124, Office Action, mailed Jan. 16, 2009, 10 pages.
U.S. Appl. No. 11/725,287, Office Action, mailed Jun. 12, 2009, 5 pages.
U.S. Appl. No. 11/725,287, Office Action, mailed Dec. 3, 2008, 7 pages.
U.S. Appl. No. 12/175,182, Office Action, mailed Sep. 3, 2009, 7 pages.
U.S. Appl. No. 29/284,454, filed Sep. 7, 2007, entitled "Implantable Port Device," issued Aug. 12, 2008 as U.S. Patent No. D574,950, 8 pages.
U.S. Appl. No. 29/284,456, filed Sep. 7, 2007 entitled "Implantable Port Device," 8 pages.

U.S. Appl. No. 60/658,518, filed Mar. 4, 2005, publicly accessible Oct. 5, 2006, 62 pages.
"Extravasation of Radiologic Contrast." PA-PSRS Patient Safety Advisory—vol. 1, No. 3, Sep. 2004, 6 pages.
Biffi, R. et al. "Best Choice of Central Venous Insertion Site for the Prevention of Catheter-Related Complications in Adult Patients Who Need Cancer Therapy: A Randomized Trial." Annals of Oncology, Jan. 29, 2009, 6 pages
Biffi, R. et al. "Use of totally implantable central venous access ports for high-dose chemotherapy and peripheral blood stem cell transplantation: results of a monocentre series of 376 patients." Annals of Oncology 15:296-300, 2004, 5 pages.
Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2011, 9 pages.
Costa, Nancy, "More Than Skin Deep: An Overview of Iodinated Contrast Media." Journal for the Association for Vascular Access, vol. 8, No. 4, 2003, 6 pages.
Costa, Nancy, "Understanding Contrast Media." Journal of Infusion Nursing, vol. 27, No. 5, Sep./Oct. 2004, 11 pages.
Extreme Access, Bard Access Systems, Inc., Product Brochure, 2003, 5 pages.
Fallscheer, et al., "Injury to the Upper Extremity Caused by Extravasation of Contrast Medium: A True Emergency." Scandinavian Journal of Plastic and Reconstructive Surgery and Hand Surgery, vol. 41, pp. 26-32, 2007, 7 pages.
Hou, Shaw-Min et al. "Comparisons of Outcomes and Survivals for Two Central Venous Access Port Systems." Journal of Surgical Oncology, 91:61-66, 2005, 6 pages.
Johnson, Kathleen A., "Power Injectable Portal Systems," Journal of Radiology Nursing, vol. 28, Issue 1, Mar. 2009, 6 pages.
LAP-BAND System Access Port Fill Guide I, "9.75/10.0 cm Lap-Band System vs. 11 cm LAP-BAND System: For Product Manufactured Prior to Jul. 2001" BioEnterics Corporation, 1 page.
Port-A-Cath P.A.S. PORT Systems by Deltec, Product Specifications, 1999, 2 pages.
Sandstede, Joern, "Pediatric CT," available online at www.multislice-ct.com, MultiSLICE-CT.com, version 02, May 2, 2003, 36 pages.
Sanelli, et al., "Safety and Feasibility of Using a Central Venous Catheter for Rapid Contrast Injection Rates." American Journal of Radiology, vol. 183, pp. 1829-1834, Dec. 2004, 6 pages.
Smith, Lisa Hartkoph, "Implanted Ports, Computer Tomography, Power Injectors, and Catheter Rupture." Clinical Journal of Oncology Nursing, vol. 12, No. 5 Oct. 2008, 4 pages.
Solomon, et al., "CIN Strategies: Anticipate, Manage, Prevent." Supplement to Imaging Economics, May 2007, 20 pages.
Steinbach, Barbara, G., Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993, 24 pages.
Sullivan et al. "Radiopaque Markers on Mammary Implants." American Journal of Roentgenology 153(2):428, Aug. 1989, 2 pages.
U.S. Food and Drug Administration, "Guidance for Institutional Review Boards and Clinical Investigators 1998 Update: Medical Devices." Version Sep. 10, 2008, 13 pages.
Vergara, et al., "Adverse Reactions to Contrast Media in CT: Effects of Temperature and Ionic Property." Radiology, vol. 199, No. 2, May 1996, 4 pages.
Vogelzang, Robert L., "Power Injection Through Central Venous Catheters: Physiological and Hemodynamic Considerations." The McGaw Medical Center of Northwestern University, Feinberg School of Medicine, 3 pages.
Wells, S. "Venous Access in Oncology and Haematology Patients: Part One." Nursing Standard, vol. 22, No. 52, pp. 39-46, Sep. 3, 2008, 9 pages.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001, 6 pages.
International Application No. PCT/US1999/028695, International Preliminary Examination Report, dated Apr. 21, 2001, 4 pages.

International Application No. PCT/US1999/028695, International Search Report, dated Apr. 11, 2000, 2 pages.
International Application No. PCT/US2006/008022, International Preliminary Report on Patentability and Written Opinion, dated Sep. 12, 2007, 6 pages.
International Application No. PCT/US2006/015695, International Preliminary Report on Patentability and Written Opinion, dated Oct. 30, 2007, 9 pages.
International Application No. PCT/US2006/016056, International Preliminary Report on Patentability and Written Opinion, dated Oct. 30, 2007, 9 pages.
International Application No. PCT/US2006/016056, International Search Report, dated Sep. 20, 2006, 4 pages.
International Application No. PCT/US2006/049007, International Preliminary Report on Patentability and Written Opinion, dated Jul. 1, 2008, 5 pages.
International Application No. PCT/US2007/006776, International Preliminary Report on Patentability, dated Mar. 6, 2008, 3 pages.
International Application No. PCT/US2007/011015, International Preliminary Report on Patentability, dated Nov. 23, 2009, 9 pages.
International Application No. PCT/US2007/011015, International Search Report, dated Jun. 10, 2008, 2 pages.
International Application No. PCT/US2007/011015, Written Opinion, dated Jun. 10, 2008, 3 pages.
International Application No. PCT/US2007/011456, International Search Report, dated Aug. 28, 2008, 2 pages.
International Application No. PCT/US2007/011456, Written Opinion, dated Aug. 28, 2008, 4 pages.
International Application No. PCT/US2008/010520, International Search Report, dated Feb. 24, 2009, 2 pages.
International Application No. PCT/US2008/010520, Written Opinion, dated Feb. 24, 2009, 4 pages.
International Application No. PCT/US2008/078976, International Search Report and Written Opinion, dated Apr. 3, 2009, 6 pages.
International Application No. PCT/US2009/062854, International Search Report, dated Dec. 23, 2009, 2 pages.
U.S. Appl. No. 11/320,223, Office Action, mailed Jan. 21, 2010, 8 pages.
U.S. Appl. No. 11/368,954, Interview Summary Communication from the USPTO, mailed May 12, 2010, 3 pages.
U.S. Appl. No. 11/368,954, Office Action, mailed Jan. 27, 2010, 7 pages.
U.S. Appl. No. 11/380,124, Office Action, dated Apr. 26, 2010, 7 pages.
U.S. Appl. No. 11/380,124, Office Action, dated Sep. 21, 2009, 8 pages.
U.S. Appl. No. 11/380,621, Office Action, dated Jan. 14, 2010, 17 pages.
U.S. Appl. No. 11/380,621, Office Action, dated Jul. 1, 2009, 16 pages.
U.S. Appl. No. 11/380,621, Office Action, dated Jun. 6, 2008, 16 pages.
U.S. Appl. No. 11/725,287, Notice of Allowance, dated Aug. 29, 2009, 4 pages.
U.S. Appl. No. 11/725,287, Notice of Withdrawal from Issue, dated Oct. 23, 2009, 1 page.
U.S. Appl. No. 11/725,287, Office Action, dated Mar. 29, 2010.
U.S. Appl. No. 11/725,287, Response, filed Feb. 24, 2009, 9 pages.
U.S. Appl. No. 11/725,287, Response, filed Jul. 28, 2009, 4 pages.
U.S. Appl. No. 11/725,287, Response, filed Sep. 29, 2010, 10 pages.
U.S. Appl. No. 12/023,280, Office Action, dated Jul. 23, 2009, 11 pages.
U.S. Appl. No. 12/023,280, Office Action, dated Oct. 5, 2009, 9 pages.
U.S. Appl. No. 12/175,182, Office Action, dated Feb. 22, 2010, 6 pages.
U.S. Appl. No. 12/175,182, Office Action, dated Jul. 22, 2010, 7 pages.
U.S. Appl. No. 12/175,182, Response, filed Dec. 3, 2009, 13 pages.
U.S. Appl. No. 12/175,182, Response, filed Jun. 22, 2010, 14 pages.
U.S. Appl. No. 12/175,182, Response, filed Jan. 24, 2011, 13 pages.
U.S. Appl. No. 12/175,182, Notice of Allowability, mailed Mar. 9, 2011, 5 pages.
U.S. Appl. No. 12/175,270, Office Action, dated Jan. 5, 2011, 6 pages.
U.S. Appl. No. 12/419,957, Office Action, dated Jun. 30, 2009, 6 pages.
U.S. Appl. No. 12/419,957, Office Action, mailed Feb. 18, 2010, 6 pages.
U.S. Appl. No. 12/420,007, Office Action, dated Feb. 18, 2010, 9 pages.
U.S. Appl. No. 12/420,007, Office Action, dated Jul. 14, 2009, 7 pages.
U.S. Appl. No. 29/247,954, Notice of Allowability, dated Jul. 30, 2007, 3 pages.
U.S. Appl. No. 29/247,954, Office Action, dated Apr. 6, 2007, 6 pages.
U.S. Appl. No. 11/725,287, Office Action, dated Dec. 7, 2011, 4 pages.
U.S. Appl. No. 11/725,287, Response, filed Jan. 6, 2011, 10 pages.
U.S. Appl. No. 11/725,287, Supplemental Response and Suggestion of Interference, filed Feb. 18, 2011, 64 pages.
Plinski, et al., "Implantable Cardioverter-Defibrillators: Implications for the Nonelectrophysiologist." Annals of Internal Medicine, Abstract of vol. 122 No. 10, pp. 770-777, May 15, 1995, 3 pages.
Thistlethwaite et al., "Generalized Feature-Based RSA of Orthopaedic Implants." 2003 Summer Bioengineering Conference, Jun. 25-29, Sonesta Beach Resort in Key Biscayne, Florida, 2 pages.
U.S. Appl. No. 11/725,287, Response, mailed Oct. 11, 2011, 5 pages.
U.S. Appl. No. 11/725,287, Declaration of Interference, mailed Nov. 10, 2011, 6 pages.
U.S. Appl. No. 11/725,287, Office Action, mailed Oct. 5, 2011, 6 pages.
U.S. Appl. No. 11/725,287, Supplemental Response and Suggestion of Interference, filed May 26, 2011, 62 pages.
U.S. Appl. No. 12/175,270, Response, filed Jan. 17, 2012, 10 pages.
U.S. Appl. No. 12/175,270, Office Action, dated May 26, 2011, 6 pages.
U.S. Appl. No. 12/175,270, Office Action, dated Sep. 14, 2011, 6 pages.
U.S. Appl. No. 12/175,270, Response, filed Apr. 5, 2011, 7 pages.
U.S. Appl. No. 12/175,270, Response, filed Aug. 22, 2011, 18 pages.

* cited by examiner

VENOUS ACCESS PORT WITH MOLDED AND/OR RADIOPAQUE INDICIA

RELATED APPLICATIONS

This application claims benefit of U.S. Provisional Application Ser. No. 60/936,491, filed Jun. 20, 2007, entitled "Venous Access Port With Molded And/Or Radiopaque Indicia," which is incorporated herein by reference.

FIELD OF THE INVENTION

This invention relates generally to medical devices, and more particularly to venous access ports having integrally molded and/or radiopaque indicia.

BACKGROUND OF THE INVENTION

Venous access ports for the infusion and/or withdrawal of fluids from a patient are well-known, secured to the proximal end of an implanted catheter. These ports are typically used for drug infusion or for withdrawal of small amounts of blood, where large flows of fluid are not required. The ports are assemblies of a needle-impenetrable housing with a discharge port in fluid communication with the catheter and the reservoir within the port housing, and provide a subcutaneous self-sealing septum that defines an access site for multiple needle sticks through the covering skin tissue of the patient, through the septum and into the reservoir, without the need to continuously search for new access sites. Examples of such ports are disclosed, for example, in U.S. Pat. Nos. 4,704,103; 4,762,517; 4,778,452; 5,185,003; 5,213,574 and 5,637,102.

It is desired to provide a venous access port assembly that provides a medical practitioner with capability to discern an important property of the port assembly after the port assembly has been implanted into a patient.

BRIEF SUMMARY OF THE INVENTION

The present invention is directed to an implantable venous access port having a marking visible by X-ray examination, providing identification on the X-ray of characteristics of the implanted access port. These characteristics might otherwise be unknown once the port is implanted under the skin of the patient. Considering that X-ray examination is normal practice prior to medical access of the port, an X-ray examination that also identifies important characteristics of an implanted port is beneficial to the practitioner.

Accordingly, the present invention is the incorporation of a molded marking into or onto the venous access port, or the addition of radiopaque indicia onto the access port, and/or the addition of radiopaque indicia onto a molded marking integrated into the access port, all of which would be discernable under X-ray examination to provide information concerning a characteristic or attribute of the venous access port, so that a practitioner, subsequent to implantation of the access port under the skin of a patient, can determine that characteristic or attribute of the port by X-ray examination.

One such characteristic could be power injectable capability; that is, an indication that the venous access port is rated for the power injection of contrast fluid. Power injection capability can be indicated with the letters "CT," for "computed tomography", or "contrast enhanced computed tomography." "CT" would indicate the access port's capability to withstand high pressures used during injection of contrast fluid into a patient, and the letters "CT" would be understood in medical practice to indicate that the port is suitable for the high pressure injection of contrast fluid. Naturally, any characteristic or attribute of the venous access port could be indicated, and any choice of letters or symbols could be employed.

In one embodiment, an access port of the present invention includes a housing and a septum, providing an interior reservoir and a passageway extending from the reservoir through a stem of a discharge port to establish fluid communication with a proximal end of a catheter lumen to which the port assembly is secured prior to placement of the assembly into a patient. The port may optionally have more than one reservoir and associated septum. The housing could include molded therein the letters "CT." If the housing is made of a plastic material, such as a silicone elastomer, the letters "CT" (or the entire housing) could be loaded with a radiopaque agent, allowing the letters "CT" (or the entire housing) to be seen by X-ray examination. If the housing comprises a metal material, or if the portion of the housing including the letters "CT" is made of a metal material, the letters would naturally be visible by X-ray examination.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Certain terminology is used herein for convenience only and is not to be taken as a limitation on the present invention.

The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1 to 4 includes a housing 12 and a septum 14, with a discharge port 16 extending from a distal end 18 of the port assembly 10 to be attached securely and sealingly to the proximal end of a catheter (not shown). A passageway 20 extends from the interior reservoir 22 to the distal tip opening 24 of discharge port 16. A recess 26 is seen to be provided along both sides of discharge port 16, facilitating insertion of the discharge port 16 into the catheter lumen and providing a clearance for a locking sleeve or clamp (not shown) utilized to compress the catheter lumen wall against the exterior surface of the discharge port 16 for assured sealed connection of the catheter with the port assembly 10.

With reference now to FIGS. 3 to 7, the interior of the port assembly 10 is shown to provide an interior reservoir 22. Housing 12 is shown to include a housing base 28 of needle-impenetrable material that includes a well 30 having a bottom floor 32 and side walls 34 that define the interior reservoir 22 beneath septum 14. Bottom floor 32 may be convex or elevated (not shown) toward the center of the reservoir, if desired. Housing base 28 includes a base flange 36 extending radially outwardly from the bottom of well 30, and base flange 36 includes openings 38,40 that serve to enable suturing to the patient upon placement of the venous access port and the attached catheter into the patient.

Figure 1:
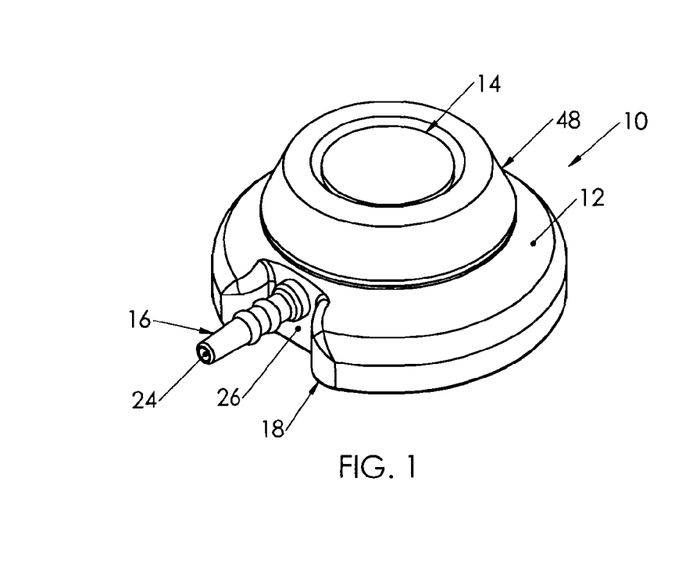
FIG. 1 is an isometric view of one embodiment of a venous access port of the present invention.
Figure 2:
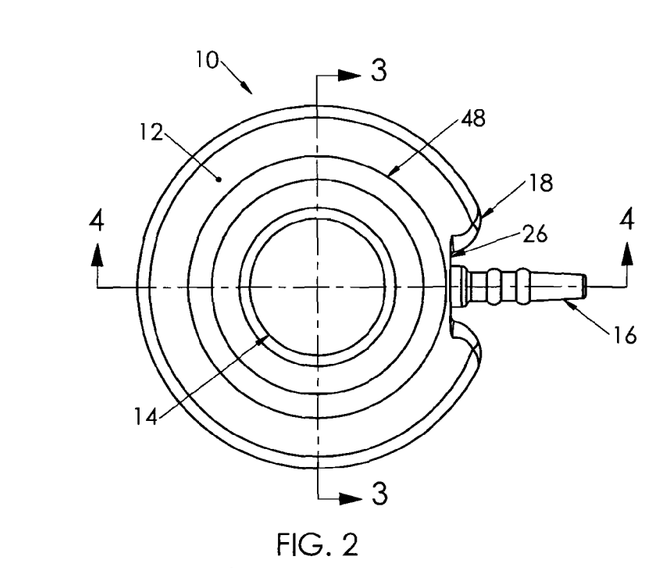
FIG. 2 is a plan view of the port of FIG. 1.
Figure 3:
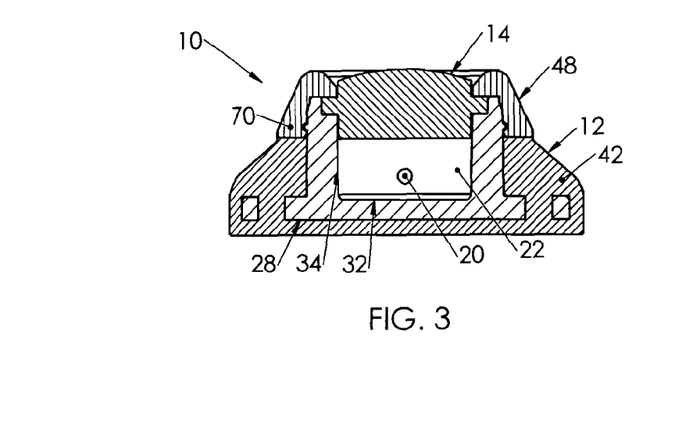
FIGS. 3 and 4 are cross-section views of the port of FIGS. 1 and 2 taken along lines 3-3 and lines 4-4 of FIG. 2, respectively.
Figure 4:
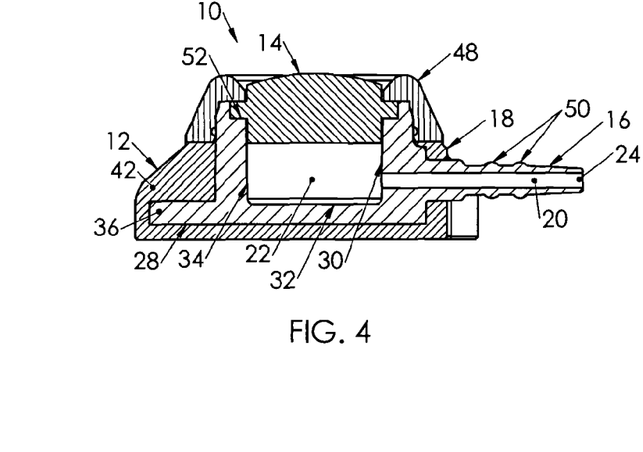
Figure 5:
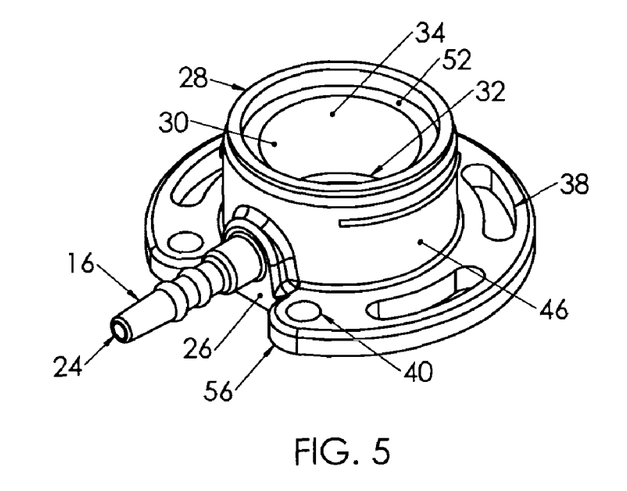
FIG. 5 is an isometric view of a needle-impenetrable housing base of the venous access port of FIG. 1.
Figure 6:
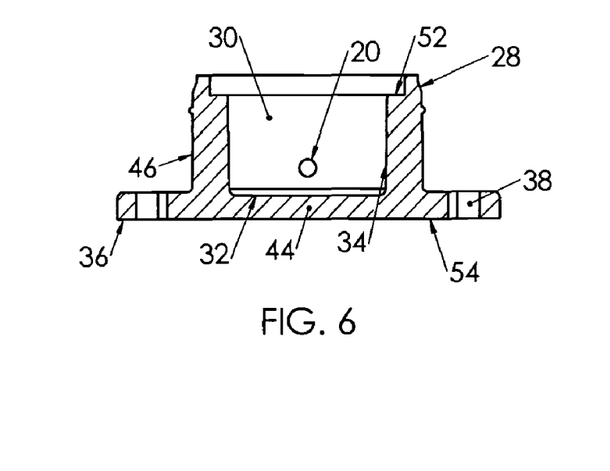
FIGS. 6 and 7 are transverse cross-sectional and longitudinal cross-sectional views of the housing base of FIG. 5.

As shown in FIGS. 3 and 4, a skirt 42 is overmolded about housing base 28 and may be of silicone elastomer. It is seen that skirt 42 encapsulates the outer surfaces of the bottom wall 44 and the bottom portion of the side walls 46 of housing base 28, and is shown to fill in the suture holes 38,40; but since the material is silicone elastomer, suturing is possible since the suturing needle can easily be inserted through the material of skirt 42 and through the suture holes, and thereafter the filled openings provide minimal opportunity for ingrowth of patient tissue into the openings.

Figure 7:
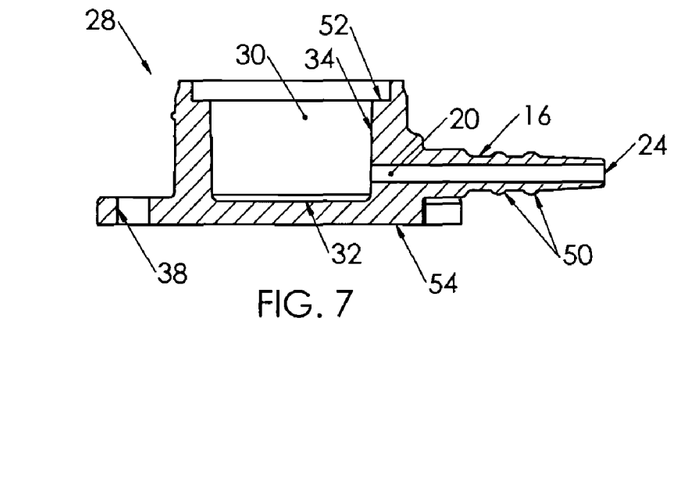

Also seen in FIGS. 1 to 4 is cap 48, which secures to housing base 28 to in turn secure septum 14 in position in the port assembly 10. Preferably, skirt 42 is insert molded onto base flange 36 of housing base 28 after cap 48 is secured to the upper portion of housing base 28 to secure the septum in position. It is seen in FIGS. 4 and 7 that discharge port 16 is integral with housing base 28 as is preferable. Discharge port 16 is shown to have a pair of annular ridges 50 that facilitate with the mechanical connection of the catheter proximal end with the port assembly 10. Housing base 28 includes a septum seat 52 extending into the top of well 30, into which a flange of the septum will be seated, preferably under radially inward compression. Housing base 28 has a bottom outer surface 54.

Figure 8:
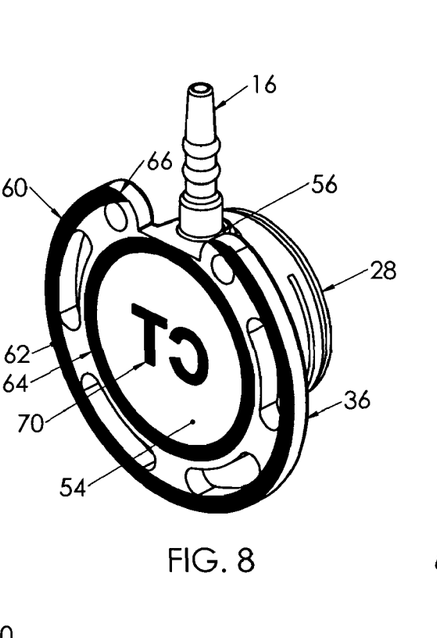
FIG. 8 is an isometric view from below of one embodiment of the housing base of FIG. 5, showing radiopaque indicia applied on the housing base bottom surface.
Figure 9:
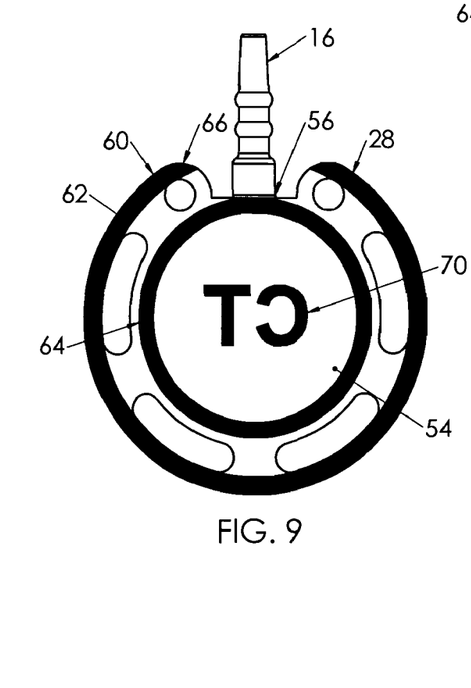
FIGS. 9 and 10 are bottom and top views of the housing base of FIG. 8 having radiopaque indicia thereon, with the top view (FIG. 10) being analogous to a X-ray view of the venous access port seen by a radiologist, with indicia visible by X-ray shown by dashed lines in FIG. 10.
Figure 10:
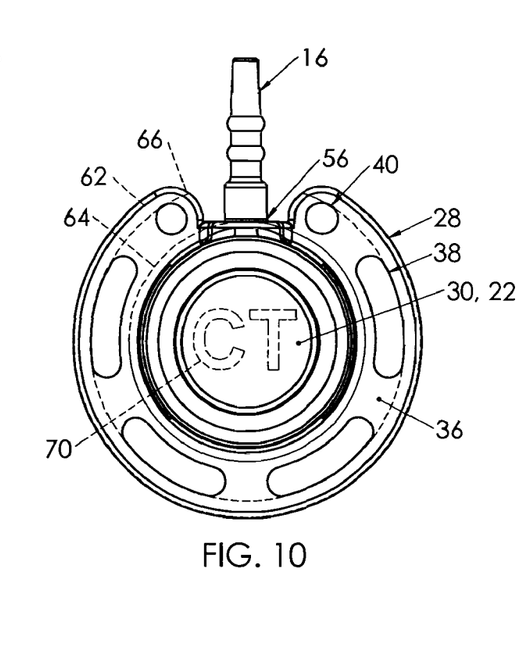

Radiopaque markings 60 of the present invention are shown in FIGS. 8 to 10. A larger outer circle 62 is seen provided on the outermost periphery of bottom base surface 54, and a smaller inner circle 64 is seen provided within the area circumscribed by the suture openings 38 and holes 40 through base flange 36. Adjacent to discharge port 16, a recess 56 is provided in the skirt of the housing base to provide a clearance for use of a connection sleeve that will be used to secure the catheter (not shown), and outer circle 62 is shown to have a gap 66 at the recess. Outer and inner circles or rings 62,64 circumscribe radiopaque indicia 70.

Radiopaque indicia 70 are provided on bottom outer surface 54 within the region directly beneath the reservoir and septum. In the example shown, indicia 70 comprise the letters "CT" (FIG. 10) representing the term "computed tomography." The meaning of this particular example of indicia is that the venous access port assembly 10 is rated for high pressure injection such as is necessary for infusion into the patient of contrast medium that is used in computed tomography. Other indicia may of course be used that indicate some other attribute or characteristic of the venous access port assembly. The radiopaque markings and indicia would appear on an X-ray of the patient, and the indicia are provided in a mirror-image orientation on the bottom outer surface of the housing base (FIGS. 7 and 8) so that the indicia would appear as "CT" when the X-ray is viewed (FIG. 9), easily discerned by the radiologist or technologist. Centering of the indicia within the region (identified as "30,22" in FIG. 10) directly beneath the reservoir and septum minimizes any obscuring by the structure of the venous access port assembly, and the indicia may also be easily discernable should the port assembly be at an angle from the horizontal plane of the X-ray; the outer and inner circles 62,64 would appear oval or elliptical should the port assembly be at such an angle. Gap 66 in outer circle 62 would also appear and would indicate the location of the discharge port stem 16.

The radiopaque markings may constitute marking fluid that is embossed or imprinted or otherwise applied onto the surface of the housing base 28, such as black radiopaque ink Part No. C11002 Rev A formulated by Creative Imprinting of Erie, Pa., from Marabu Tampapur TPU 910 clear with tungsten added, available from Marabuwerke GmbH & Co. KG of Stuttgart, Germany, and may be applied on plasma-treated surfaces. At least the housing base 28, the septum 14 and the skirt 42 are of radiotransparent or radiolucent material as is well known in implanted medical devices, and the housing base may be molded of polysulfone resin.

The radiopaque markings may alternatively applied to the inwardly facing surface of the bottom wall of the housing base, or may constitute foil or film (such as a decal) of radiopaque material embedded within the housing base, these alternatives not being shown in the drawings.

Figure 11:
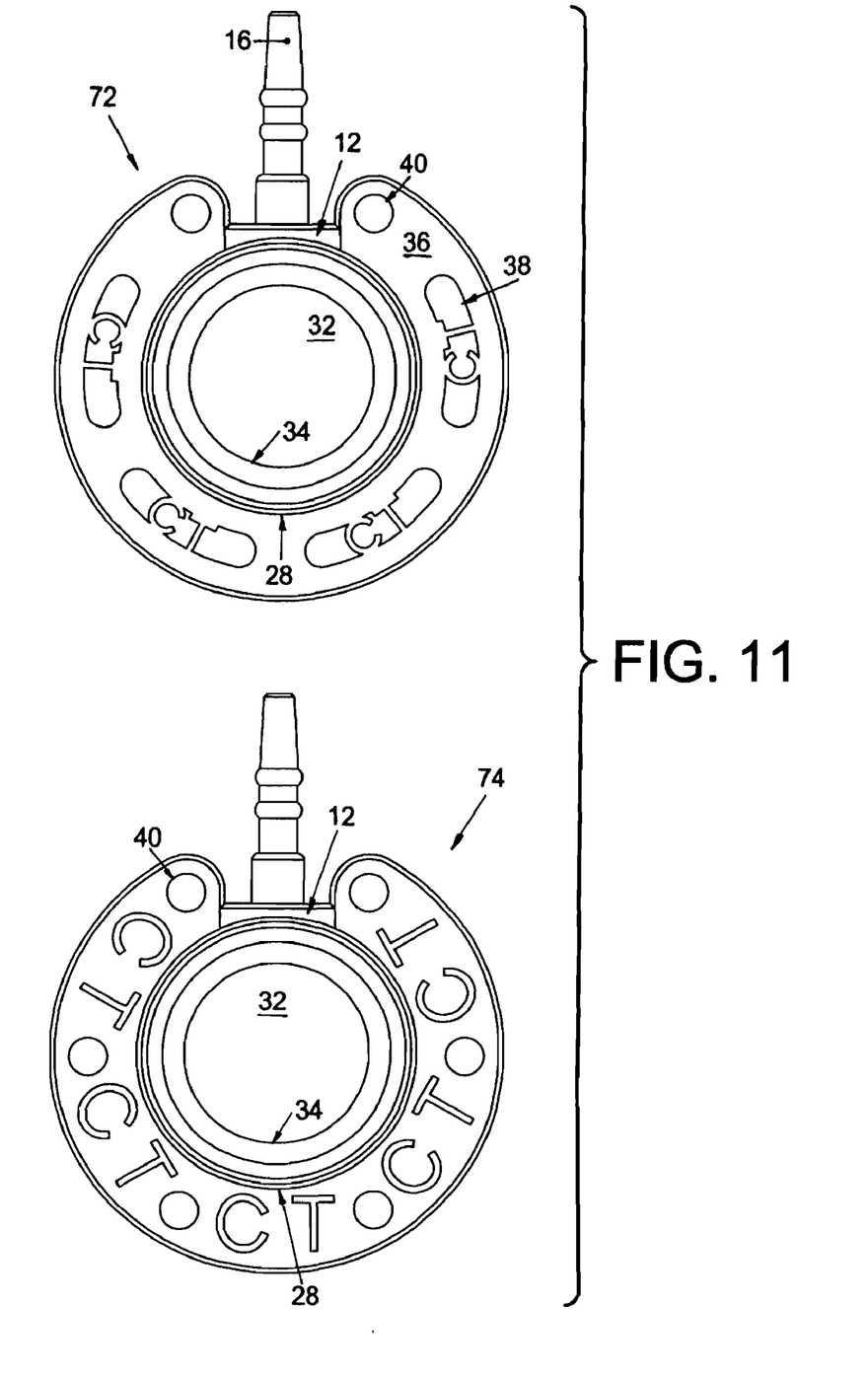
FIG. 11 illustrates top views of two alternative embodiments of the needle-impenetrable housing base of the venous access port of FIG. 1, showing integrally molded "CT" markings.
Figure 12:
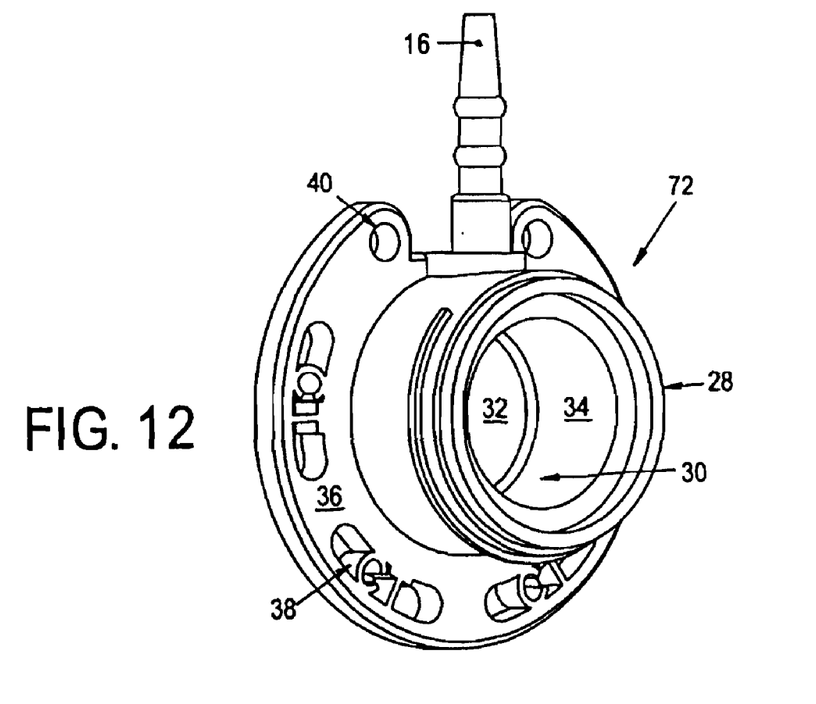
FIG. 12 illustrates an isometric view of one of the FIG. 11 embodiments of the needle-impenetrable housing base of the venous access port of FIG. 1, featuring an integrally molded "CT" marking where the letters "CT" are formed of housing material.
Figure 13:
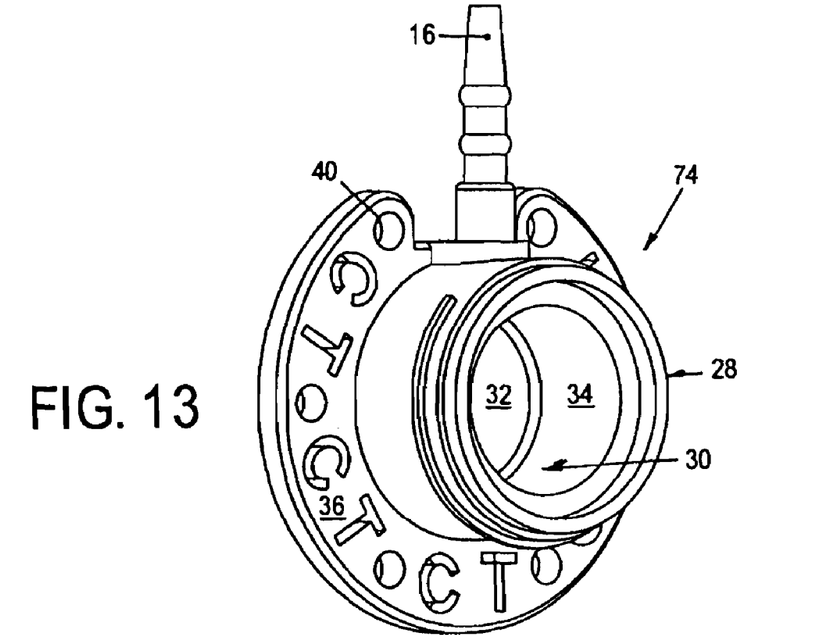
FIG. 13 illustrates an isometric view of the other of the FIG. 11 embodiments of the needle-impenetrable housing base of the venous access port of FIG. 1, featuring an integrally molded "CT" marking where the letters "CT" comprise voids in the housing material, as if cut or punched out of the housing material.

FIG. 11 illustrates top views of two alternative embodiments 72, 74 of the needle-impenetrable housing base 28 of the venous access port 10 of the present invention. Each of the alternative embodiments 72, 74 shows "CT" markings integrally formed in the base flange 36 of the housing base 28. The first alternative embodiment 72, an isometric view of which is illustrated in FIG. 12, features integrally molded "CT" markings within the suture openings 38, where the letters "CT" are formed of the base flange 36 material. The second alternative embodiment 74, an isometric view of which is illustrated in FIG. 13, features integrally molded "CT" markings alongside the suture openings 38, 40, where the markings are voids in the base flange 36 material, as if cut or punched out of the base flange 36 material. Naturally, the markings could be configured elsewhere within or about the housing base 28, or within a peripheral portion of another component of the venous access port 10.

If the housing base 28 is made of a plastic material, such as a silicone elastomer or polysulfone resin, the letters "CT," or the base flange 36, or the entire housing base 28, could be applied with a radiopaque agent or fluid, allowing the applied area to be visible by X-ray examination. If the housing base 28 is comprised of a metal material, or if the base flange 36, or a portion thereof, is comprised of metal (particularly the letters "CT"), those portions would naturally be visible by X-ray examination without application of the radiopaque agent.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A venous access port assembly for implantation into a patient, comprising:
    a housing comprising a base defining a bottom wall of at least one reservoir, a discharge port extending from the at least one reservoir, and a flange adjacent to the at least one reservoir, the flange comprising a height extending from a top surface of the flange to a bottom surface of the flange, the flange further comprising X-ray discernable indicia configured to indicate, under X-ray examination, that the port assembly is rated for power injection, the X-ray discernable indicia located in the flange and extending through the height of the flange from the top surface of the flange to the bottom surface of the flange so that the X-ray discernable indicia are visually discernable to a naked eye from both the top surface of the flange and the bottom surface of the flange prior to implantation of the port assembly; and
    a needle-penetrable septum communicating with the housing.

2. The assembly of claim 1, wherein the X-ray discernable indicia comprise radiopaque markings.

3. The assembly of claim 2, wherein the radiopaque markings comprise radiopaque marking fluid.

4. The assembly of claim 3, wherein the fluid contains tungsten.

5. The assembly of claim 1, wherein the flange is comprised of a metal material, whereby the indicia are visible by X-ray examination when the assembly is subcutaneously implanted in a patient.

6. The assembly of claim 1, wherein the flange extends outwardly from the base about a perimeter of the at least one reservoir.

7. The assembly of claim 1, wherein the flange further includes suture openings, and the indicia are located within predetermined suture openings.

8. The assembly of claim 1, wherein the indicia comprise flange material.

9. The assembly of claim 1, wherein the indicia are voids in the flange.

10. The assembly of claim 1, wherein the assembly is at least partially comprised of radiotransparent material.

11. The assembly of claim 1, wherein the indicia indicate, under X-ray examination, that the assembly is adapted to withstand high pressures used for injection of contrast fluid.

12. An implantable venous access port assembly comprising:
    a needle-penetrable septum;
    a housing securing the needle-penetrable septum, the housing comprising a housing base defining at least one reservoir, and a flange extending radially from the housing base, the flange comprising:
        X-ray discernable material;
        a height extending from a top surface of the flange to a bottom surface of the flange; and
        one or more cutouts extending entirely through the height of the flange from the top surface of the flange to the bottom surface of the flange, the one or more cutouts comprising one or more voids in the X-ray discernable material, the one or more cutouts configured to indicate, under X-ray examination, that the port assembly is rated for power injection, the one or more cutouts further configured to be visually discernable to a naked eye from both the top surface of the flange and the bottom surface of the flange prior to implantation of the port assembly; and
    a discharge port extending from the housing.

13. The port assembly of claim 12, wherein the flange comprises the X-ray discernable material and the one or more cutouts extend entirely through the X-ray discernable material from the top surface of the flange to the bottom surface of the flange.

14. The port assembly of claim 12, wherein the top surface and the bottom surface of the flange are coated with the X-ray discernable material.

15. The port assembly of claim 12, wherein the one or more cutouts are further configured to indicate, under X-ray examination, that the port assembly is rated to be used for power injection of contrast fluid.

16. The port assembly of claim 12, wherein the one or more cutouts are further configured to indicate, under X-ray examination, that the port assembly is adapted to withstand high pressures used for injection of contrast fluid.

17. An implantable venous access port assembly comprising:
    a needle-penetrable septum;
    a housing securing the needle-penetrable septum, the housing comprising a housing base defining at least one reservoir, and a flange extending radially from the housing base, the flange comprising:
        a height extending from a top surface of the flange to a bottom surface of the flange;
        one or more X-ray discernable indicia formed in the flange and extending through the height of the flange from the top surface of the flange to the bottom surface of the flange, the one or more X-ray discernable indicia configured to indicate, under X-ray examination, that the port assembly is rated for power injection, the one or more X-ray discernable indicia further configured to be visually discernable to a naked eye from both the top surface of the flange and the bottom surface of the flange prior to implantation of the port assembly; and
    a discharge port extending from the housing.

18. The port assembly of claim 17, wherein the flange further comprises one or more cutouts disposed about peripheries of the one or more X-ray discernable indicia.

19. The port assembly of claim 18, wherein:
    the flange comprises X-ray discernable material extending entirely through the height of the flange from the top surface of the flange to the bottom surface of the flange,
    the one or more X-ray discernable indicia extend entirely through the X-ray discernable material from the top surface of the flange to the bottom surface of the flange, and
    the one or more cutouts extend entirely through the X-ray discernable material from the top surface of the flange to the bottom surface of the flange.

20. The port assembly of claim 18, wherein:
    the top surface and the bottom surface of the flange are coated with the X-ray discernable material.

21. The port assembly of claim 17, wherein the one or more X-ray discernable indicia are further configured to indicate, under X-ray examination, that the port assembly is rated to be used for power injection of contrast fluid.

22. The port assembly of claim 17, wherein the one or more X-ray discernable indicia are further configured to indicate, under X-ray examination, that the port assembly is adapted to withstand high pressures used for injection of contrast fluid.

* * * * *

UNITED STATES PATENT AND TRADEMARK OFFICE
CERTIFICATE OF CORRECTION

PATENT NO.           : 8,257,325 B2
APPLICATION NO.      : 12/143377
DATED                : September 4, 2012
INVENTOR(S)          : Timothy M. Schweikert et al.

It is certified that error appears in the above-identified patent and that said Letters Patent is hereby corrected as shown below:

Column 4, Lines 31-32, replace "Creative Imprinting of Erie, Pa." with --CI Medical, Inc. of Norton, Ma.--

Signed and Sealed this
Fifth Day of February, 2013

Teresa Stanek Rea
*Acting Director of the United States Patent and Trademark Office*